US010182824B2

(12) United States Patent
Monti et al.

(10) Patent No.: US 10,182,824 B2
(45) Date of Patent: Jan. 22, 2019

(54) CLIP APPLICATOR

(71) Applicant: AtriCure, Inc., Mason, OH (US)

(72) Inventors: Matthew Monti, Cincinnati, OH (US); Kenneth Lance Miller, Hamilton, OH (US); Philip P. Resig, Mason, OH (US); Salvatore Privitera, Mason, OH (US); Jason Iain Glithero, McDonough, GA (US); Adam Harp, Cincinnati, OH (US); James David Hughett, Sr., Acworth, GA (US)

(73) Assignee: AtriCure, Inc., Mason, OH (US)

( * ) Notice: Subject to any disclaimer, the term of this patent is extended or adjusted under 35 U.S.C. 154(b) by 250 days.

(21) Appl. No.: 14/138,275

(22) Filed: Dec. 23, 2013

(65) Prior Publication Data
US 2015/0173767 A1 Jun. 25, 2015
US 2016/0151070 A9 Jun. 2, 2016

Related U.S. Application Data

(63) Continuation of application No. 12/944,430, filed on Nov. 11, 2010, now Pat. No. 8,636,754.

(51) Int. Cl.
*A61B 17/128* (2006.01)
*A61B 17/122* (2006.01)
(Continued)

(52) U.S. Cl.
CPC ...... *A61B 17/1285* (2013.01); *A61B 17/1227* (2013.01); *A61B 2017/2926* (2013.01);
(Continued)

(58) Field of Classification Search
CPC ............ A61B 17/1227; A61B 17/1285; A61B 2019/2234; A61B 2017/2926; Y10T 24/44256; Y10T 29/49826
See application file for complete search history.

(56) References Cited

U.S. PATENT DOCUMENTS

| 3,818,784 A | 6/1974 | McClure |
| 5,108,420 A | 4/1992 | Marks |

(Continued)

FOREIGN PATENT DOCUMENTS

| WO | 1993015791 | 8/1993 |
| WO | 1998018389 | 5/1998 |

(Continued)

*Primary Examiner* — Son Dang
(74) *Attorney, Agent, or Firm* — Dorton and Willis, LLP; Ryan Willis

(57) ABSTRACT

An occlusion assembly comprising: (a) a tissue occlusion device comprising a first linear clamping portion and a second linear clamping portion, the first and second linear clamping portions oriented to overlap and be parallel to one another in a clamped position, the tissue occlusion device further including a spring concurrently coupled to and interposed by the first and second linear clamping portions to bias the first and second linear clamping portions toward the clamped position; and, (b) an endoscopic rein coupled to the tissue occlusion device and configured to facilitate repositioning of the tissue occlusion device toward an occlusion position where the first and second linear clamping portions are interposed by tissue, where the endoscopic rein includes a flexible wire coupled to the clamping device and configured to facilitate repositioning of the tissue occlusion device toward the occlusion position.

12 Claims, 5 Drawing Sheets

(51) Int. Cl.
 *A61B 17/29* (2006.01)
 *A61B 34/30* (2016.01)
(52) U.S. Cl.
 CPC ... *A61B 2034/305* (2016.02); *Y10T 24/44256* (2015.01); *Y10T 29/49826* (2015.01)

(56) References Cited

U.S. PATENT DOCUMENTS

| | | |
|---|---|---|
| 5,190,541 A | 3/1993 | Abele et al. |
| 5,282,811 A | 2/1994 | Booker et al. |
| 5,282,844 A | 2/1994 | Stokes |
| 5,403,311 A | 4/1995 | Abele et al. |
| 5,403,343 A | 4/1995 | Sugarbaker |
| 5,575,795 A | 11/1996 | Anderson |
| 5,643,255 A | 7/1997 | Organ |
| 5,643,291 A | 7/1997 | Pier et al. |
| 5,676,636 A | 10/1997 | Chin |
| 5,702,411 A | 12/1997 | Back et al. |
| 5,709,224 A | 1/1998 | Behl et al. |
| 5,727,569 A | 3/1998 | Benetti et al. |
| 5,735,848 A | 4/1998 | Yates et al. |
| 5,766,217 A | 6/1998 | Christy |
| 5,797,960 A | 8/1998 | Stevens et al. |
| 5,823,956 A | 10/1998 | Roth et al. |
| 5,827,216 A | 10/1998 | Igo et al. |
| 5,827,306 A | 10/1998 | Yoon |
| 5,843,152 A | 12/1998 | Tu et al. |
| 5,849,019 A | 12/1998 | Yoon |
| 5,891,162 A | 4/1999 | Sugarbaker et al. |
| 6,016,452 A | 1/2000 | Kasevich |
| 6,019,722 A | 2/2000 | Spence et al. |
| 6,077,261 A | 6/2000 | Behl et al. |
| 6,080,173 A | 6/2000 | Williamson |
| 6,152,936 A | 11/2000 | Christy et al. |
| 6,161,543 A | 12/2000 | Cox et al. |
| 6,203,541 B1 | 3/2001 | Keppel |
| 6,237,605 B1 | 5/2001 | Vaska et al. |
| 6,241,727 B1 | 6/2001 | Tu et al. |
| 6,248,124 B1 | 6/2001 | Pedros et al. |
| 6,258,105 B1 | 7/2001 | Hart et al. |
| 6,277,065 B1 | 8/2001 | Donofrio |
| 6,315,715 B1 | 11/2001 | Taylor et al. |
| 6,322,494 B1 | 11/2001 | Bullivant et al. |
| 6,328,688 B1 | 12/2001 | Borst et al. |
| 6,334,843 B1 | 1/2002 | Borst et al. |
| 6,336,898 B1 | 1/2002 | Borst et al. |
| 6,340,344 B1 | 1/2002 | Christopher |
| 6,357,100 B2 | 3/2002 | Speller, Jr. et al. |
| 6,464,700 B1 | 10/2002 | Koblish et al. |
| 6,465,196 B1 | 10/2002 | Hobbs et al. |
| 6,494,211 B1 | 12/2002 | Boyd et al. |
| 6,520,974 B2 | 2/2003 | Tanner et al. |
| 6,562,051 B1 | 5/2003 | Bolduc et al. |
| 6,584,360 B2 | 6/2003 | Francischelli et al. |
| 6,645,196 B1 | 11/2003 | Nixon et al. |
| 6,666,861 B1 | 12/2003 | Grabek |
| 6,679,268 B2 | 1/2004 | Stevens et al. |
| 6,701,929 B2 | 3/2004 | Hussein |
| 6,709,442 B2 | 3/2004 | Miller et al. |
| 6,712,804 B2 | 3/2004 | Roue et al. |
| 6,719,767 B1 | 4/2004 | Kimblad |
| 6,872,210 B2 | 3/2005 | Hearn |
| 6,955,175 B2 | 10/2005 | Stevens et al. |
| 6,955,643 B2 | 10/2005 | Gellman et al. |
| 6,960,218 B2 | 11/2005 | Rennich |
| 6,981,628 B2 | 1/2006 | Wales |
| 7,008,401 B2 | 3/2006 | Thompson et al. |
| 7,011,669 B2 | 3/2006 | Kimblad |
| 7,033,378 B2 | 4/2006 | Smith et al. |
| 7,044,134 B2 | 5/2006 | Khairkhahan et al. |
| 7,056,294 B2 | 6/2006 | Khairkhahan et al. |
| 7,077,851 B2 | 7/2006 | Lutze et al. |
| 7,207,997 B2 | 4/2007 | Shipp et al. |
| 7,209,783 B2 | 4/2007 | Fellows et al. |
| 7,424,965 B2 | 9/2008 | Racenet et al. |
| 7,473,261 B2 | 1/2009 | Rennich |
| 7,527,634 B2 | 5/2009 | Zenati et al. |
| 7,572,266 B2 | 8/2009 | Young et al. |
| 7,644,848 B2 | 1/2010 | Swayze et al. |
| 7,892,244 B2 | 2/2011 | Monassevitch et al. |
| 7,896,895 B2 | 3/2011 | Boudreaux et al. |
| 8,313,508 B2 | 11/2012 | Belson et al. |
| 8,636,754 B2 | 1/2014 | Hughett et al. |
| 9,017,349 B2 | 4/2015 | Privitera et al. |
| 9,393,023 B2 | 7/2016 | Privitera et al. |
| 2001/0039419 A1 | 11/2001 | Francischelli et al. |
| 2002/0111647 A1 | 8/2002 | Khairkhahan et al. |
| 2004/0064138 A1 | 4/2004 | Grabek |
| 2005/0277959 A1* | 12/2005 | Cosgrove ............... A61B 17/12 606/151 |
| 2006/0212049 A1 | 9/2006 | Mohiuddin |
| 2006/0253129 A1 | 11/2006 | Liddicoat et al. |
| 2006/0271089 A1 | 11/2006 | Alejandro et al. |
| 2007/0016228 A1 | 1/2007 | Salas |
| 2007/0021761 A1 | 1/2007 | Phillips |
| 2007/0027456 A1 | 2/2007 | Gartner et al. |
| 2007/0149988 A1 | 6/2007 | Michler et al. |
| 2008/0125795 A1 | 5/2008 | Kaplan et al. |
| 2008/0208324 A1 | 8/2008 | Glithero et al. |
| 2009/0012545 A1* | 1/2009 | Williamson, IV ... A61B 17/083 606/157 |
| 2009/0069823 A1 | 3/2009 | Foester et al. |
| 2009/0253961 A1 | 10/2009 | Le et al. |
| 2010/0004663 A1 | 1/2010 | Murphy et al. |
| 2010/0204716 A1 | 8/2010 | Stewart et al. |
| 2011/0046437 A1* | 2/2011 | Kassab ................. A61F 5/0086 600/37 |
| 2011/0152922 A1 | 6/2011 | Jeong |
| 2012/0109161 A1* | 5/2012 | Privitera ............ A61B 17/1227 606/142 |

FOREIGN PATENT DOCUMENTS

| | | |
|---|---|---|
| WO | 1998024488 | 6/1998 |
| WO | 1999013785 | 3/1999 |
| WO | 1999013936 | 3/1999 |
| WO | 2006009729 | 1/2006 |
| WO | 2007127664 | 11/2007 |
| WO | 2013025841 | 2/2013 |
| WO | 2013110089 | 7/2013 |

\* cited by examiner

CLIP APPLICATOR

CROSS REFERENCE TO RELATED APPLICATIONS

This application is a continuation of nonprovisional patent application Ser. No. 12/944,430, filed Nov. 11, 2010, now U.S. Pat. No. 8,636,754, the disclosure of which is incorporated herein by reference.

RELATED ART

Field of the Invention

The present invention is directed to applicators for clamps and, more specifically, for applicators that may be utilized in minimally invasive procedures to position and apply the occlusion clamps.

INTRODUCTION TO THE INVENTION

It is a first aspect of the present invention to provide a removable deployment device for a clamp comprising: (a) a first retainer bar including a line coupled thereto; (b) a second retainer bar including a second line coupled thereto, where the first retainer bar is coupled to the second retainer bar.

In a more detailed embodiment of the first aspect, the first retainer bar includes a first depression on its exterior surface, and the first line extends across the first depression. In yet another more detailed embodiment, the second retainer bar includes a second depression on its exterior surface, and the second line extends across the second depression. In a further detailed embodiment, the first retainer bar includes a projection extending therefrom, the projection including a crucifix. In still a further detailed embodiment, the second retainer bar includes a projection extending therefrom, the projection including a first segment extending perpendicularly from the second retainer bar, and a second segment including a hook mounted to the first segment.

In yet another more detailed embodiment of the first aspect, the second retainer bar includes a projection extending therefrom, the projection including a hook. In yet another more detailed embodiment of the first aspect, the engagement feature may be a hole into or through one or both retaining bars. In still another more detailed embodiment, the first retainer bar includes a first through hole, the second retainer bar includes a second through hole, and a third line is concurrently received within the first through hole and the second through hole to couple the first and second retainer bars. In a further detailed embodiment, an extraction tab is coupled to the third line. In still a further detailed embodiment, at least one of the first line, the second line, and the third line comprises a suture. In a more detailed embodiment, the first line comprises a first suture, the second line comprises a second suture, and the third line comprises a third suture.

It is a second aspect of the present invention to provide a clamp assembly comprising: (a) a clamp including at least first and second elongate clamping portions biased toward one another; (b) a first retainer bar including a first line removably coupling the first retainer bar to the first elongate clamping portion; (c) a second retainer bar including a second line removably coupling the second retainer bar to the second elongate clamping portion, where the first retainer bar is coupled to the second retainer bar.

In a more detailed embodiment of the second aspect, the first retainer bar includes a first depression on its exterior surface, and the first line extends across the first depression. In yet another more detailed embodiment, the second retainer bar includes a second depression on its exterior surface, and the second line extends across the second depression. In a further detailed embodiment, the first retainer bar includes a projection extending therefrom, the projection including a crucifix. In still a further detailed embodiment, the second retainer bar includes a projection extending therefrom, the projection including a first segment extending perpendicularly from the second retainer bar, and a second segment including a hook mounted to the first segment. In a more detailed embodiment, the second retainer bar includes a projection extending therefrom, the projection including a hook.

In yet another more detailed embodiment of the second aspect, the first retainer bar includes a first through hole, the second retainer bar includes a second through hole, and the third line is concurrently received within the first through hole and the second through hole. In still another more detailed embodiment, an extraction tab is coupled to the first and second retainer bars. In a further detailed embodiment, at least one of the first line, the second line, and the third line comprises a suture. In still a further detailed embodiment, the first line comprises a first suture, the second line comprises a second suture, and the third line comprises a third suture. In a more detailed embodiment, the clamp comprises a first and second elongate clamping portions respectively having ends coupled together with respective resilient urging members configured to urge the first and second elongate clamping portions toward one another. In a more detailed embodiment, the clamp further comprises a fabric covering over the first and second elongate clamping portions.

It is a third aspect of the present invention to provide a method of fabricating a clamp comprising: (a) mounting a first retainer bar to a first elongate clamping portion of a clamp using a first line, the clamp also including a second elongate clamping portion, where the first and second elongate clamping portions are biased toward one another; (b) mounting a second retainer bar to the second elongate clamping portion of the clamp using a second line; (c) mounting the first retainer bar to the second retainer bar, where the first and second elongate clamping portions each include proximal and distal longitudinal ends, where the proximal longitudinal ends are coupled to a first spring, and where the distal longitudinal ends are coupled to a second spring.

In a more detailed embodiment of the third aspect, the first line comprises a suture. In yet another more detailed embodiment, mounting the first retainer bar to the first elongate clamping portion includes looping the first line around the first elongate clamping portion and tying the first line to the first retainer bar, and mounting the second retainer bar to the second elongate clamping portion includes looping the second line around the second elongate clamping portion and tying the second line to the second retainer bar. In a further detailed embodiment, tying the first line to the first retainer bar includes forming a plurality of half hitch knots, and tying the second line to the second retainer bar includes forming a plurality of half hitch knots. In still a further detailed embodiment, tying the first line to the first retainer bar includes forming a timberline knot, and tying the second line to the second retainer bar includes forming a timberline knot. In a more detailed embodiment, mounting the first retainer bar to the second retainer bar includes using a third line coupled to both the first retainer bar and the second retainer bar. In a more detailed embodiment, the first elongate clamping portion and the second elongate clamping portion are coupled together using at least one line. In a more detailed embodiment, at least one of the first retainer bar and the second retainer bar includes a crucifix projection adapted to be gripped by endoscopic graspers. In another more detailed embodiment, the first retainer bar includes a first projection adapted to be gripped by endoscopic graspers, where the first projection is directed away from the clamp, and the second retainer bar includes a second projection adapted to be gripped by endoscopic graspers, where the second projection is directed away from the clamp. The endoscopic graspers may be manual or robotically driven.

It is a fourth aspect of the present invention to provide a clamp assembly comprising: (a) a clamping device biased toward a closed position; (b) a first retainer bar removably coupled to the clamping device; (c) a second retainer bar removably coupled to the clamping device, where the first retainer bar and the second retainer bar are oriented in parallel to one another and, where the first retainer bar and the second retainer bar each include an engagement feature to facilitate grasping by a grasping device.

In a more detailed embodiment of the fourth aspect, the first retainer bar includes a first depression on its exterior surface, the first retainer bar includes a first line removably coupling the first retainer bar to the clamping device and, the first line extends across the first depression. In yet another more detailed embodiment, the second retainer bar includes a second depression on its exterior surface, the second retainer bar includes a second line removably coupling the second retainer bar to the clamping device and, the second line extends across the second depression. In a further detailed embodiment, the first retainer bar includes a projection extending therefrom, the projection including a crucifix. In still a further detailed embodiment, the second retainer bar includes a projection extending therefrom, the projection including a first segment extending perpendicularly from the second retainer bar, and a second segment including a hook mounted to the first segment. In a more detailed embodiment, the second retainer bar includes a projection extending therefrom, the projection including a hook.

In yet another more detailed embodiment of the fourth aspect, the first retainer bar includes a first through hole, the second retainer bar includes a second through hole and, a line is concurrently received within the first through hole and the second through hole. In still another more detailed embodiment, the clamp assembly includes an extraction tab coupled to the line. In a further detailed embodiment, at least one of the first retainer bar and the second retainer bar is removably coupled to the clamping device using a suture. In still a further detailed embodiment, the first retainer bar is removably coupled to the clamping device using a first suture and, the second retainer bar is removably coupled to the clamping device using a second suture. In a more detailed embodiment, the clamping device comprises a first and second elongate clamping portions respectively having ends coupled together with respective resilient urging members configured to urge the first and second elongate clamping portions toward one another. In a more detailed embodiment, the clamping device further comprises a fabric covering over the first and second elongate clamping portions.

It is a fifth aspect of the present invention to provide a clamp assembly comprising: (a) a clamping device biased toward a closed position; (b) a first retainer bar removably coupled to the clamping device; (c) a second retainer bar removably coupled to the clamping device and, where the first retainer bar and the second retainer bar are oriented in parallel to one another.

In a more detailed embodiment of the fifth aspect, at least one of the first retainer bar and the second retainer bar includes a line to removably couple at least one of the first retainer bar and the second retainer bar to the clamping device. In yet another more detailed embodiment, the line lies across a cutting zone. In a further detailed embodiment, the cutting zone comprises a depression formed within an exterior of the least one of the first retainer bar and the second retainer bar. In still a further detailed embodiment, the line comprises at least one of a suture, a cable, a strap, and a thread. In a more detailed embodiment, at least one of the engagement features includes a projection. In a more detailed embodiment, the projection comprises at least one of a cruciform and a hook. In another more detailed embodiment, each engagement feature includes a projection and, the projection of the first retainer bar is different from the projection of the second retainer bar. In yet another more detailed embodiment, at least one of the engagement features includes a through hole. In still another more detailed embodiment, the engagement feature of the first retainer bar includes a through hole and, the engagement feature of the second retainer bar includes a through hole.

In yet another more detailed embodiment of the fifth aspect, the first retainer bar is coupled to the second retainer bar using a retainer. In still another more detailed embodiment, the retainer comprises a line. In a further detailed embodiment, the line comprises at least one of a suture and a cable. In still a further detailed embodiment, the first retainer bar and the second retainer bar each include an engagement feature to facilitate grasping by a grasping device. In a more detailed embodiment, at least one of the first retainer bar and the second retainer bar includes a line to retrieve the retainer bar post decoupling at least one of the first retainer bar and the second retainer bar from the clamping device. In a more detailed embodiment, the clamping device comprises a first and second elongate clamping portions respectively having ends coupled together with respective resilient urging members configured to urge the first and second elongate clamping portions toward one another. In another more detailed embodiment, the clamping device further comprises a fabric covering over the first and second elongate clamping portions. In yet another more detailed embodiment, the clamping assembly further comprises at least one limiting line coupled to the clamping device, wherein the clamping device comprises a first and second elongate clamping portions configured to move toward and away from one another, the at least one limiting line limiting how far the first and second elongate clamping portions can move away from one another. In still another more detailed embodiment, the at least one limiting line is coupled to the first and second retainer bars. In still a further more detailed embodiment, the at least one limiting line is coupled to the first and second elongate clamping portions. In yet a further more detailed embodiment, the at least one limiting line is further coupled to the clamping device to continue the coupling of the at least one limiting line with the first and second elongate clamping portions.

As used herein, the term "line" means or includes a tether such as, without limitation, a cable, a string, a thread, and/or a suture.

As used herein, the term "grasper" means any device capable of grasping or gripping and includes, without limitation, endowrist jawed devices such as endoscopic graspers, minimally invasive graspers, tongs, and forceps.

DETAILED DESCRIPTION

Figure 1:
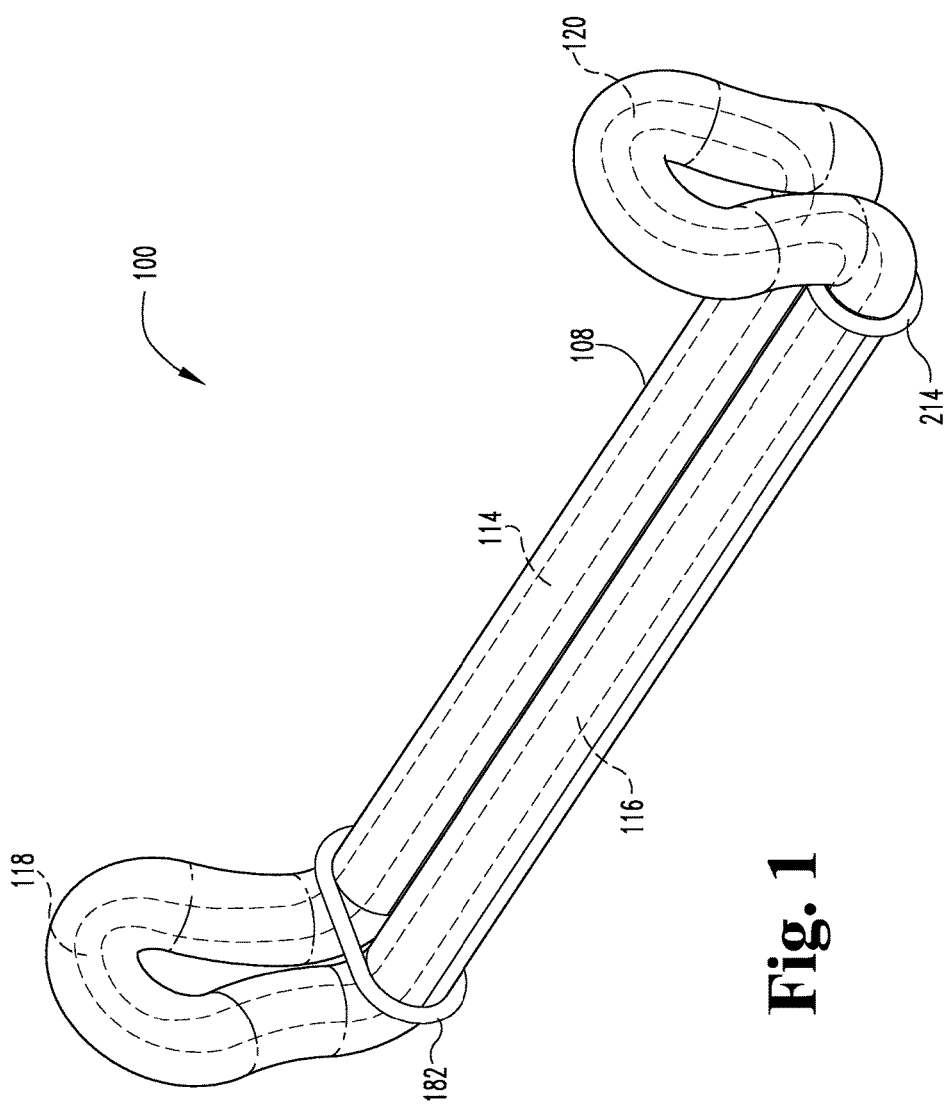
FIG. 1 is an elevated perspective view of an exemplary occlusion clamp in accordance with the present disclosure.
Figure 2:
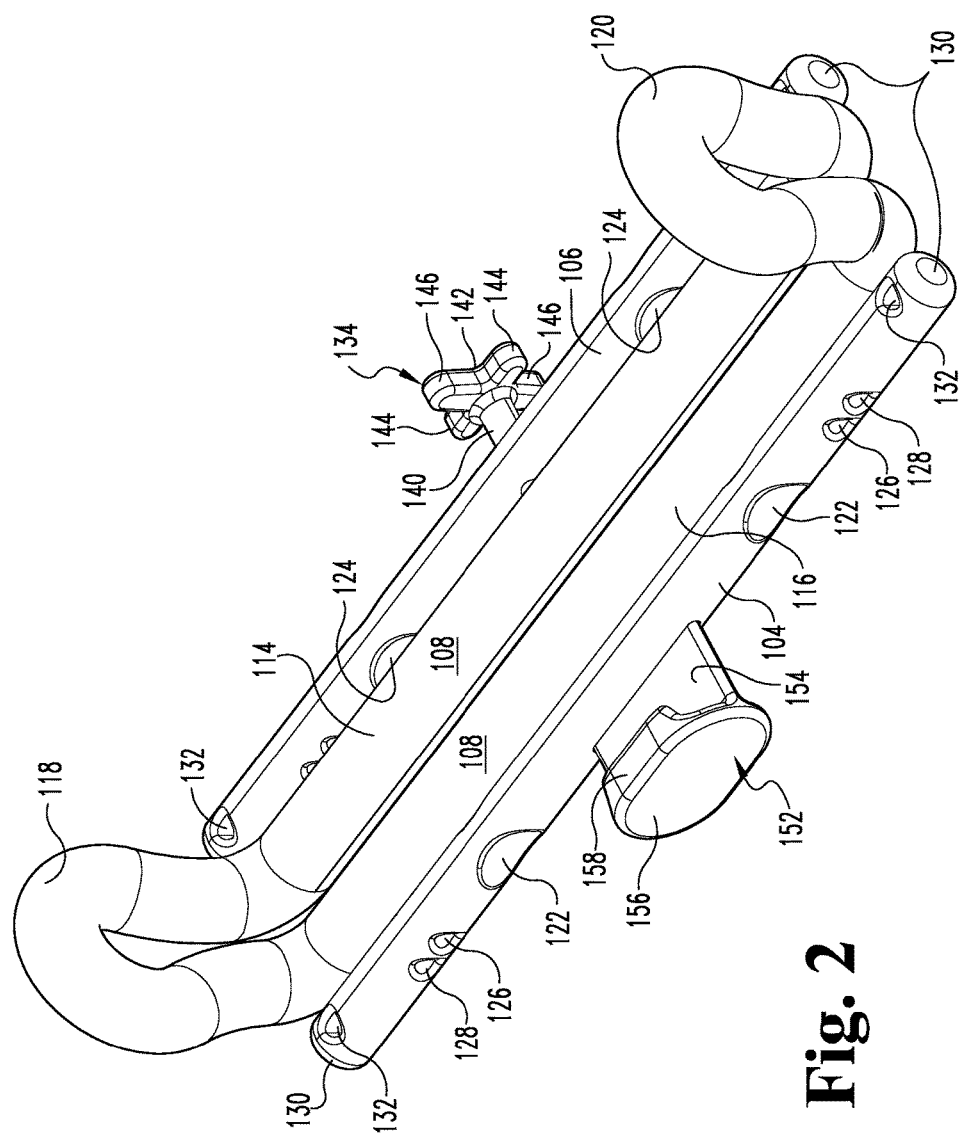
FIG. 2 is an elevated perspective view of the exemplary occlusion clamp of FIG. 1 with a pair of exemplary retainer bars.
Figure 3:
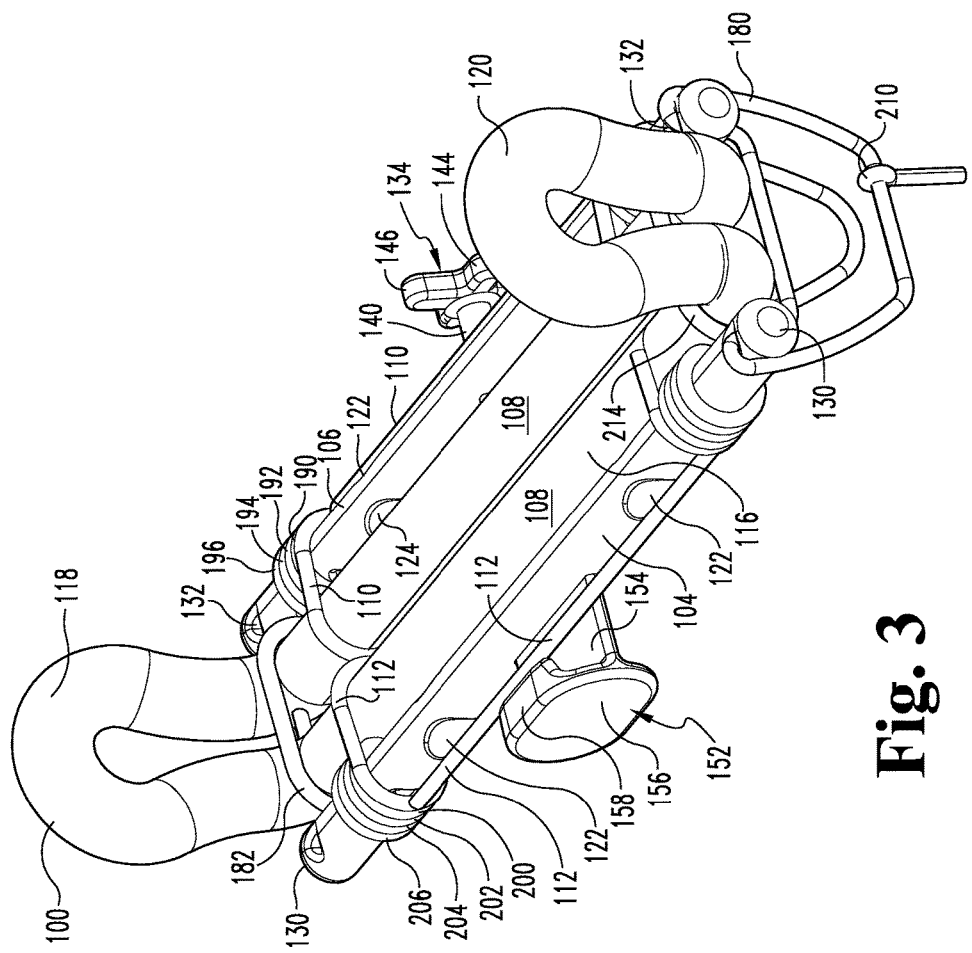
FIG. 3 is an elevated perspective view of the exemplary occlusion clamp and exemplary retainer bars of FIG. 2 being coupled together using lines.

The exemplary embodiments of the present invention are described and illustrated below to encompass methods and devices for opening and closing clamps/clips such as, without limitation, occlusion clamps. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Referencing FIGS. 1-5, an exemplary occlusion clamp 100, as shown and described in U.S. patent application Ser. No. 11/994,725, filed on Jul. 8, 2008, the disclosure of which is incorporated herein by reference, includes an applicator assembly 102 in order to reposition and deploy the occlusion clamp. The exemplary applicator assembly 102 includes a pair of retainer bars 104, 106 mounted to a fabric cover material 108 using sutures 110, 112. In this exemplary embodiment, the fabric cover material 108 may be made of a material such as polyester having been sewn around the clamping portions 114, 116 and the urging members 118, 120.

Each retainer bar 104, 106 includes complementary depressions 122, 124 formed into the circumferential surface on opposite sides at two different longitudinal locations. Two primary through holes 126, 128 are longitudinally outset from each set of depressions 122, 124 and extend perpendicularly through the bar 104, 106. The bars 104, 106 can contain more or less than two through holes. These primary through holes 126, 128 are also centered from side to side with respect to the diameter of the retainer bars 104, 106 so that the central axis of each hole intersects the central, longitudinal axis of the retainer bar. More specifically, each primary through hole 126, 128 includes complementary top and bottom openings that are on the same sides as the depressions 122, 124. In other words, the rounded sides of the retainer bars 104, 106 that are offset approximately ninety degrees from the depressions 122, 124 are also offset approximately 90 degrees from the top and bottom openings of each primary through hole 126, 128. Inset from the ends 130 of each retainer bar 104, 106 are secondary through holes 132 extending perpendicularly through the bar and are centered from side to side. But these secondary through holes 132 are perpendicular with respect to, but do not intersect, the primary through holes 126, 128. As with the primary through holes 126, 128, the secondary through holes 132 also have opposed top and bottom openings. As will be discussed in more detail below, the holes 126, 128 accommodate sutures 110, 112 to couple the bars 104, 106 to the occlusion clamp 100.

Figure 4:
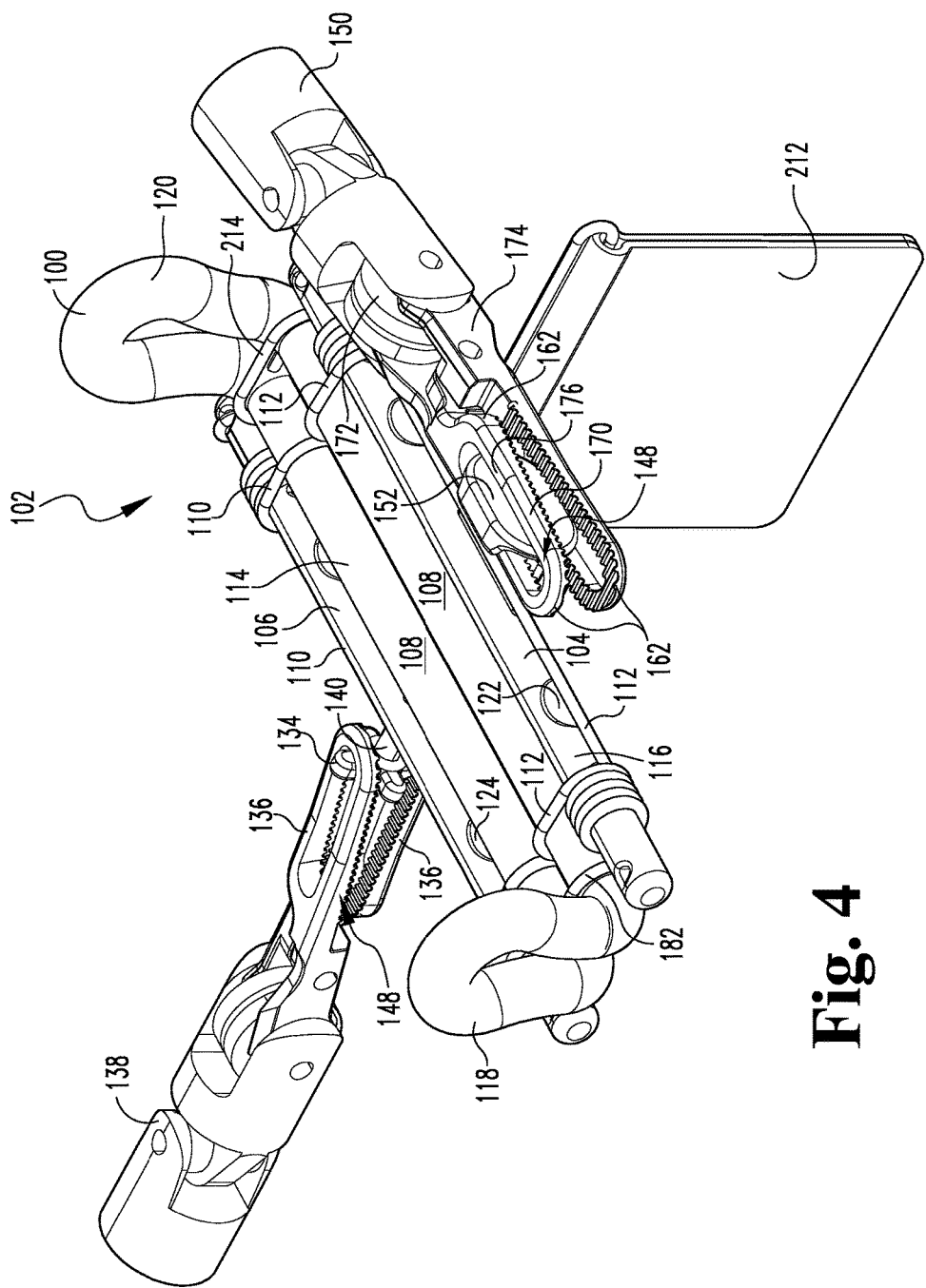
FIG. 4 is an elevated perspective view of an exemplary occlusion clamp and applicator assembly, along with a partial view of a pair of endoscopic graspers.
Figure 5:
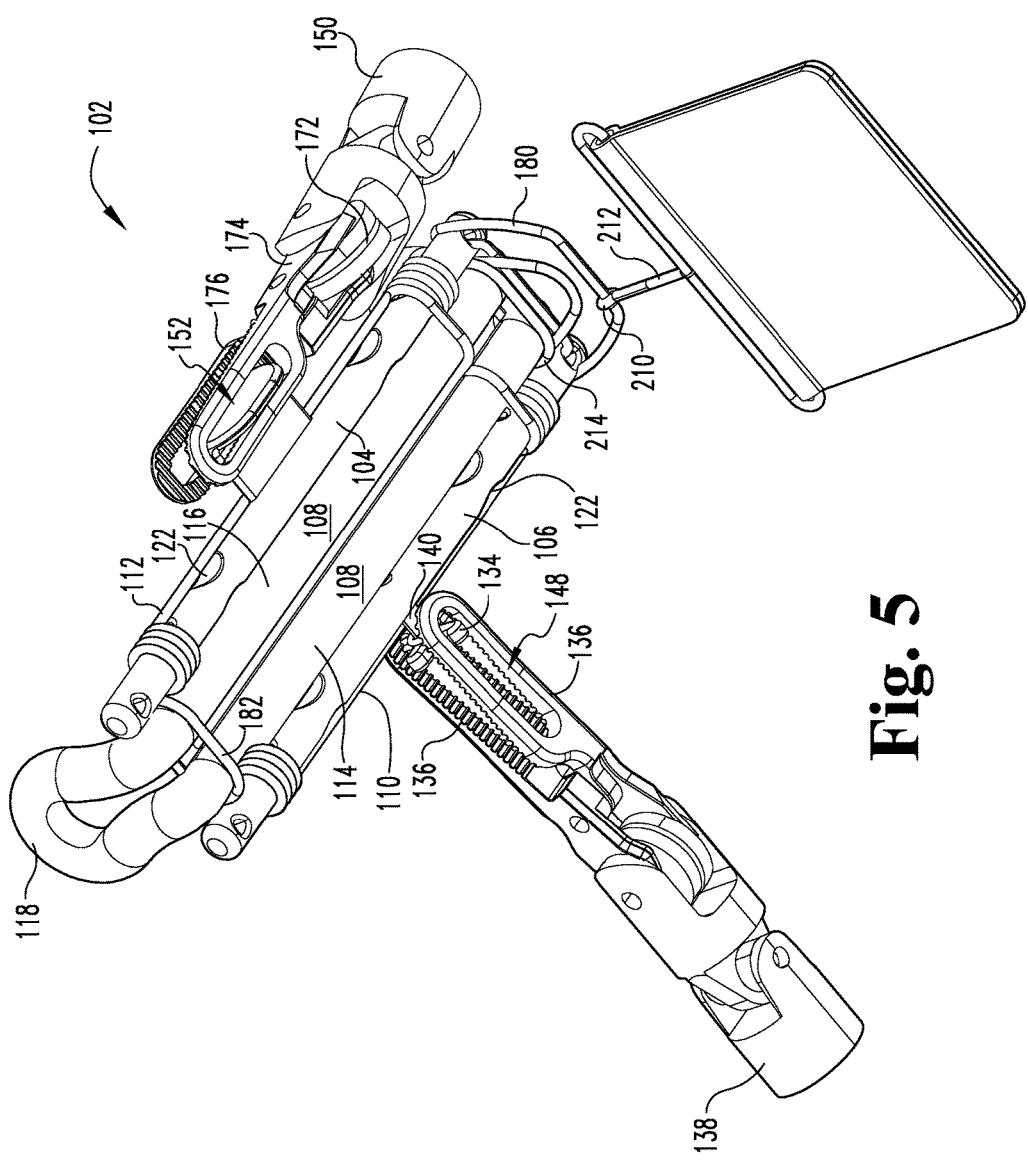
FIG. 5 is an underneath, perspective view of the exemplary occlusion clamp and applicator assembly, along with a partial view of a pair of endoscopic graspers, of FIG. 4.

While the retainer bars 104, 106 are similar, there are some distinct differences between the two. For example, the retainer bars 104, 106 need not be exact compliments or mirrors of each other. In this exemplary embodiment, the second retainer bar 106 includes a projection 134 shaped to conform to the jaws 136 of a first endoscopic grasper 138. An exemplary endoscopic grasper 138 that may be used coincident with the applicator assembly 102 includes, without limitation, the da Vinci surgical system available from Intuitive Surgical, Inc. (www.intuitivesurgical.com/products/davinci_surgicalsystem/index.aspx). This projection 134 extends perpendicularly away from the retainer bar 106 in a direction opposite the occlusion clamp 100. In this exemplary embodiment, the projection 134 extends from the same side of the retainer bar 106 as where the depressions 122 are formed. The projection 134 includes a cylindrical post 140 having mounted thereto a crucifix 142. The crucifix is oriented so that one set of coaxial projections 144 is parallel to the longitudinal axis of the retainer bar 106, while a second set of coaxial projections 146 is perpendicular to the longitudinal axis. The length of the post 140 allows the jaws 136 of the endoscopic grasper 138 to sandwich the first set of coaxial projections 144, while the second set of coaxial projections 146 extend through a respective oblong opening 148 of each endoscopic grasper 136. In particular, as shown in FIG. 4, the shape of the crucifix 142 is well suited for gripping by the jaws 136 and accommodating tension forces when the jaws 136 are repositioned to open the occlusion clamp 100 while a second endoscopic grasper 150 is coupled to the first retainer bar 104. It should also be noted that the retainer bars 104, 106 can be of varying or equivalent cross-sectional geometry.

The first retainer bar 104 may differ from the second retainer bar 106 in the shape of its projection 152. The projection 152 includes a longitudinal flange 154 having a perpendicular end plate 156 that is tapered and rounded over at its ends to form a pair of stops 158. These stops 158 generally face the longitudinal flange 154 and are oriented toward the retainer bar 104, thereby forming a pair of hooks. In other words, the projection includes a T-shaped cross-section and extends perpendicularly away from the retainer bar 104 in a generally opposite direction from the other projection 134. In this exemplary embodiment, the longitudinal flange 154 is generally rectangular in shape and is dimensioned to allow for gripping by the jaws 162 of the second endoscopic grasper 150. An exemplary endoscopic grasper 150 that may be used coincident with the applicator assembly 102 includes, without limitation, the da Vinci surgical system available from Intuitive Surgical, Inc. (www.intuitivesurgical.com/products/davinci_surgicalsystem/index.aspx).

By way of example, the jaws 136, 162 of the endoscopic graspers 138, 150 comprise a pair of individual jaws 170 pivoting around a common axis. Each jaw 170 includes a cylindrical base 172 having a bar 174 coupled to an oblong frame 176 extending perpendicularly away from the bar. The oblong frame 176 outlines the central opening 148 and is serrated on one side to facilitate gripping. As is shown in the figures, two of the jaws 170 are stacked upon one another so that the cylindrical bases 172 are aligned to be coaxial. In an exemplary configuration, the jaws 170 are oriented so that the oblong openings 148 overlap one another when the jaws 136, 162 are closed. Because of the openings 148 in the jaws 170, the jaws are able to receive portions of the projections 134, 152 and capable of exerting tensile forces against aspects of the projections in addition to possibly exerting compressive (i.e., gripping) forces on the projections.

Referring back to FIGS. 3, 4 and 5, the end plate 156 is dimensioned to extend far enough beyond the longitudinal flange 154 to accommodate the jaws 162 on opposing sides. Likewise, the height of the stops 158 and the tapered nature of the stops are dimensioned to pass into the through opening of one of the jaws 170. As will be discussed in more detail below, the jaws 162 of the second endoscopic grasper 150 grip the projection 152 and pull the projection in a direction generally opposite to the direction of the first endoscopic grasper 138 pulling on the first projection 134. This action operates to open the occlusion clamp 100.

Five distinct sutures 110, 112, 180, 182, 214 are utilized as part of the applicator assembly 102. The first suture 110 is coupled to the second retainer bar 106, while the other second suture 112 is coupled to the first retainer bar 104. In contrast, the third suture 180 is concurrently mounted to corresponding near ends of the first retainer 104 and the second retainer bar 106. The fourth suture 182 loosely circumscribes the clamping portions 114, 116 and is mounted to at least one of the clamping portions in close proximity to the urging member 118 using a subordinate suture (not shown). The fifth suture 214 also loosely circumscribes the clamping portions and is mounted to at least one of the clamping portions in close proximity to the urging member 120 using a subordinate suture (not shown). Both the fourth and fifth sutures are adapted to remain attached to the clamping portions 114, 116 post clamp 100 deployment. As will be discussed in more detail below, the third suture 180 is adapted to remain attached to the retainer bars 104, 106 in order to withdraw the retainer bars after the occlusion clamp 100 has been positioned to sandwich the appropriate tissue. Conversely, the first and second sutures are adapted to be severed to disengage the retainer bars 104, 106 from the occlusion clamp 100 post positioning. The cutting zones for severing the sutures are demarcated by the depressions 122.

In this exemplary embodiment, the manner in which the sutures 110, 112 are mounted to the retainer bars 104, 106 will now be discussed, starting with the second retainer bar 106. The second retainer bar 106 is positioned to be longitudinally parallel with the clamping portion 114 so the ends of the retainer bar are generally centered along the longitudinal length of the clamping portion 114. At the same time, the retainer bar 106 is positioned so that the projection 134 extends away from the other clamping portion 114. Likewise, the retainer bar 106 is positioned so that one opening of each of the primary through holes 126, 128 also faces toward the clamping portion 114 and the second opening of each of the primary holes faces away from the clamping portion. Finally, when the retainer bar 106 is properly positioned, the first suture 110 is concurrently attached to the retainer bar and the first clamping portion 114.

Initially, a predetermined length of suture 110 is positioned so that its midpoint is generally positioned to be on top of the cylindrical post 140 of the projection 134, with the suture being extended longitudinally to lie in parallel with the clamping portion 114. In this position, the suture 110 lies on top of the retainer bar 106 so that that suture extends across the top depressions 122. Each end of the suture 110 is then threaded through the nearest 126 of the primary holes so that the suture lies across the nearest of the two clamping portions 114, 116 (in this case, clamping portion 114). The ends of the suture 110 are then looped around the clamping portion 114 and then threaded through the farthest 128 of the primary holes and drawn taught. In this manner, the suture 110 has circumscribed the outside of the clamping portion 114. After the suture 110 is drawn taught, having been threaded through the farthest 128 of the primary holes, a first half hitch knot 190 is tied. Thereafter, a second 192 and a third 194 half hitch knots are tied in the ends of the suture 110 toward the ends of the retainer bar 106. After the three hitch knots are tied, the ends of the suture 110 are then utilized to tie a timberline knot 196, with any excess suture being removed at the end of the timberline knot. Methods of knot tying can be found in numerous resources, as can many types of knots that may be used to secure the retainer bars 104, 106 to the occlusion clamp 100 using sutures 110, 112.

An adhesive may be placed on the knots 190, 192, 194, 196 to secure the knots and eliminate or limit fraying and migration. Alternative methods of knot tying or retainer bar design may eliminate or decrease utilization of adhesives on the knots. For example, a compressive or constriction type of knot may also be used to secure the suture to the bar 104, 106. In addition, or in the alternative, heat staking or other methods of combining, lapping, and/or fixating suture-to-suture, suture-to-metal, or suture-to-plastic may be used. When the knots 190, 192, 194, 196 are completed, the suture 110 is generally taught around the retainer bar 106 and clamping portion 114 so that pulling on the retainer bar 106 away from the clamping portion 114 is operative to reposition the clamping portion 114.

The foregoing process is generally repeated for the first retainer bar 104 by positioning the retainer bar to be longitudinally parallel with the first clamping portions 116 so the ends of the retainer bar are generally centered along the longitudinal length of the clamping portion 116. At the same time, the retainer bar 104 is positioned so that the projection 152 extends away from the clamping portion 116. Likewise, the retainer bar 104 is positioned so that one opening of each of the primary through holes 126, 128 also faces toward the clamping portion 116 and a second opening of each of the primary holes faces away from the clamping portions. Finally, when the retainer bar 104 is properly positioned, the second suture 112 is attached using the following process.

Initially, a predetermined length of suture 112 is positioned so that its midpoint is generally positioned to be on top of the longitudinal flange 154 of the projection 152, with the suture being extended longitudinally to lie in parallel with the clamping portion 116. In this position, the suture 112 lies on top of the retainer bar 104 so that that suture extends across the top depressions 122. Each end of the suture 112 is then threaded through the nearest 126 of the primary holes so that the suture lies across the nearest of the two clamping portions 114, 116 (in this case, clamping portion 116). The ends of the suture 112 are then looped around the clamping portion 116 and then threaded through the farthest 128 of the primary holes and drawn taught. In this manner, the suture 112 has circumscribed the outside of the clamping portion 116. After the suture 112 is drawn taught, having been threaded through the farthest 128 of the primary holes, a first half hitch knot 200 is tied. Thereafter, a second 202 and a third 204 half hitch knots are tied in the ends of the suture 112 toward the ends of the retainer bar 104. After the three hitch knots are tied, the ends of the suture 112 are then utilized to tie a timberline knot 206, with any excess suture being removed at the end of the timberline knot. When the knots are completed, the suture 112 is generally taught around the retainer bar 104 and clamping portion 116 so that pulling on the retainer bar 104 away from the clamping portion 116 is operative to reposition the clamping portion 116.

In this exemplary embodiment, the manner in which the suture 180 is mounted to the retainer bars 104, 106 will now be discussed. The first retainer bar 104 and the second retainer bar 106 each include a secondary through hole 132 located proximate each longitudinal end. These through holes 132 are adapted to receive predetermined lengths of suture 180 in order to couple the retainer bars 104, 106 to one another. As will be discussed in more detail below, the suture 180 is not adapted to be severed, but instead remains coupled to the retainer bars 104, 106 after the sutures 110, 112 are severed to remove the retainer bars 104, 106 and remaining sutures 110, 112 attached to the retainer bars subsequent to deployment of the occlusion clamp 100.

In exemplary form, the third suture 180 is threaded through one of the secondary through holes 132 of the second retainer bar 106 so that the end of the suture extending from the opening nearest the urging member 120 is wrapped around the outside of the retainer bar 106 (and held in position) and is in proximity to the other end of the suture 180 exiting the opening facing away from the urging member 120. The end of the suture 180 exiting the opening that faces away from the urging member 120 travels across the ends of the two clamping portions 114, 116 and is threaded into the an opening of the nearest secondary through hole 132 of the first retainer bar 104, where the opening faces away from the urging member 120. When the suture 180 is threaded into this through hole 132, the end of the suture 180 travels through the hole 132 and exits nearer to the urging member 120. This free end 180 is then looped around the outside of the first retainer bar 104 and meets the other end of the suture 180 that was previously held in position to create a knot 210 to close the third suture 180, thereby forming a closed loop. In this exemplary embodiment, the third suture 180 loop is coupled to a tab 212 that provides a quickly apparent attachment point for one of the endoscopic graspers 138, 150 to grasp and withdraw the remaining sutures and retainer bars 104, 106 after the occlusion clamp 100 is deployed.

The fourth and fifth limiting lines or sutures 182, 214 are respectively loosely looped around the two clamping portions 114, 116 proximate the urging members 118, 120. A subordinate suture (not shown) is used to couple the sutures 182, 214 to the fabric cover material 108. In exemplary form, the length of the sutures 182, 214 is chosen to that when taught, the sutures operate to limit the travel of the clamping portions 114, 116. In other words, the sutures 182, 214 constrain just how far apart the clamping portions 114, 116 may be repositioned. It should be noted that the sutures may or may not be removed post occlusion clamp 100 deployment.

An exemplary deployment of the occlusion clamp 100 using the applicator assembly 102 presumes the sutures 110, 112 have been attached to the retainer bars 104, 106 as discussed above. Likewise, the exemplary deployment explanation also presumes that the sutures 180, 182, 214 have been respectively attached to the retainer bars and the clamping portions 114, 116. In exemplary form, deployment of the occlusion clamp 100 in a surgical procedure includes positioning the clamp in proximity to tissue to be clamped. Exemplary tissue that may be clamped by the occlusion clamp 100 includes, without limitation, the left atrial appendage of the heart. After the clamp 100 has been introduced proximate the tissue to be occluded, the endoscopic graspers 138, 150 are utilized to grasp the applicator assembly 102 in order to more precisely position the clamp 100.

Specifically, the jaws 136 of the first endoscopic grasper 138 are opened so that the openings 148 of each jaw overlap the coaxial projections 146 of the crucifix 142 and are thereafter shut or brought closer together to grasp the coaxial projections 144. In such an orientation, the jaws 136 of the endoscopic grasper 138 are able to pull on the crucifix 142 in a direction opposite, and coaxial with, the longitudinal direction of the cylindrical post 140. Concurrently, the jaws 162 of the second endoscopic grasper 150 are opened and oriented so that the openings 148 completely overlap the end plate 156 and stops 158. Thereafter, the jaws 162 are shut or brought closer together to grasp the longitudinal flange 154 of the projection 152. It should be noted that when the openings of the jaws 162 are oriented to completely overlap the end plate 156 and stops 158, this orientation coincides with the second endoscopic grasper 150 being oriented generally in parallel with the first retainer bar 104. After the endoscopic graspers 138, 150 have been positioned to grasp the projections 134, 152, the endoscopic graspers are repositioned to open the clamp 100.

By way of example, the second endoscopic grasper 150 may remain stationary, while the first endoscopic grasper 138 pulls on the projection 134 in a direction away from the clamp 100. This force mustered by the endoscopic graspers 138, 150 working in tandem is greater than the spring force associated with the urging members 118, 120, which results in the clamping portions 114, 116 being repositioned to create a gap therebetween. While this gap is maintained, using the relative position of the endoscopic graspers 138, 150, the clamp 100 is repositioned so that the tissue to be occluded is directed between the clamping portions 114, 116. After the tissue is placed between the clamping portions 114, 116 to the satisfaction of the surgeon, the endoscopic graspers 138 are repositioned toward one another so that the spring force of the clamping portions 114, 116 is applied to the tissue in question. Thereafter, surgical snips (not shown) are introduced, while the clamp 100 is positioned to clamp the tissue in question, to sever the sutures 110, 112. Specifically, the snips are introduced proximate the depressions 122 on each of the retainer bars 104, 106 to sever the sutures 110, 112, thereby creating a new pair of free ends for each suture. But it should be noted that the sutures 180 remain, thereby linking the retainer bars 104, 106 to one another. It is the new free ends of the sutures 110, 112 that discontinue the sutures being taught and the coupling between the retainer bars 104, 106 and the clamping portions 114, 116. In this manner, a surgeon grasps the tab 212 and pulls the retainer bars 104, 106 from the surgical region and the clamp 300. Because the tab 212 remains attached to the retainer bars 104, 106 by way of the suture 180, and because the sutures 110, 112 remain attached to the retainer bars by way of the knots 190, 192, 194, 196, 200, 202, 204, 206, pulling on the tab 212 removes concurrently removes the retainer bars and the sutures. In exemplary form, the tab 212 is adapted to be positioned at all times outside of the body cavity.

The foregoing components may be fabricated from any surgical grade material. By way of example, the retainer bars 104, 106 are fabricated from a metal, such as stainless steel, aluminum, or titanium, while the sutures can be obtained commercially from Ethicon (J&J) or fabricated for use. Whilst not necessary to use adhesive on the knots, a person skilled in knot tying may create a compressive or constrictive type of knot in order to eliminate or reduce the amount of adhesive. Adhesives for use with the foregoing exemplary embodiments may include CA, UV-CA, or other medical or non-medical grade adhesives. The projections can be of similar geometry or differing geometries. The retainer bars 104, 106 can be of varying or equivalent cross-sectional geometries.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. An occlusion assembly comprising:
    a tissue occlusion device comprising a first linear clamping portion and a second linear clamping portion, the first and second linear clamping portions oriented to overlap and be parallel to one another in a clamped position, the tissue occlusion device including a spring mounted to the first and second linear clamping portions to bias the first and second linear clamping portions toward the clamped position, the tissue occlusion device further including a fabric tube around the first and second linear clamping portions and the spring; and,
    a first endoscopic rein coupled the first linear clamping portion at opposing longitudinal locations thereof, at least one of the opposing longitudinal locations of the first linear clamping portion being proximate the spring, and a second endoscopic rein coupled to the second linear clamping portion at opposing longitudinal locations thereof, at least one of the opposing longitudinal locations of the second linear clamping portion being proximate the spring, the first and second endoscopic reins configured to facilitate repositioning of the tissue occlusion device to allow tissue to interpose the first and second linear clamping portions.

2. The occlusion assembly of claim 1, wherein the first endoscopic rein includes a rigid chassis coupled to the tissue occlusion device via a flexible wire.

3. The occlusion assembly of claim 2, wherein:
    the rigid chassis comprises a first retainer bar and a second retainer bar;
    the first retainer bar is oriented to overlap and be parallel to the first linear clamping portion; and,
    the second retainer bar is oriented to overlap and be parallel to the second linear clamping portion.

4. The occlusion assembly of claim 3, wherein the flexible wire comprises suture.

5. The occlusion assembly of claim 1, wherein:
    the first linear clamping portion is hollowed to receive a first portion of the spring;
    the second linear clamping portion is hollowed to receive a second portion of the spring; and,
    the first portion of the spring and the second portion of the spring are interconnected via a U-shaped segment of the spring.

6. An occlusion system comprising:
    a tissue occlusion clamp comprising a first clamping portion and a second clamping portion, the first and second clamping portions oriented to overlap and be parallel to one another in a clamped position, the tissue occlusion clamp including a spring mounted to the first and second clamping portions to bias the first and second clamping portions toward the clamped position, the tissue occlusion device further including a fabric tube around the first and second linear clamping portions and the spring; and,
    a first endoscopic removable connector coupled to the first clamping portion at opposing longitudinal locations thereof, at least one of the opposing longitudinal locations of the first clamping portion being proximate the spring, and a second endoscopic removable connector coupled to the second clamping portion at opposing longitudinal locations thereof, at least one of the opposing longitudinal locations of the second clamping portion being proximate the spring, the first and second endoscopic removable connectors configured to facilitate repositioning of the tissue occlusion clamp to allow tissue to interpose the first and second clamping portions.

7. The occlusion system of claim 6, wherein the first endoscopic removable connector includes a rigid chassis coupled to the tissue occlusion device via a flexible wire.

8. The occlusion system of claim 7, wherein:
    the rigid chassis comprises a first retainer bar;
    the first retainer bar is oriented to overlap and be parallel to the first linear clamping portion.

9. The occlusion system of claim 7, wherein the flexible wire comprises suture.

10. The occlusion system of claim 6, wherein:
    the first clamping portion is hollowed to receive a first portion of the spring;
    the second clamping portion is hollowed to receive a second portion of the spring; and,
    the first portion of the spring and the second portion of the spring are interconnected via a U-shaped segment of the spring.

11. An occlusion combination comprising:
    a tissue occlusion clip comprising a first beam and a second beam, the first and second beams oriented to overlap and be parallel to one another in a compressed position, the tissue occlusion clip including a spring mounted to the first and second beams to bias the first and second beams toward the compressed position, the tissue occlusion clip having at least one open end, the tissue occlusion clip further including a fabric tube around the first and second beams and the spring; and,
    an endoscopic grasper operatively coupled to a line repositionably coupled to the tissue occlusion clip proximate the spring, the endoscopic grasper configured to facilitate repositioning of the tissue occlusion clip toward an occlusion position where the first and second beams are interposed by tissue, wherein:
    the first beam is hollowed to receive a first portion of the spring;
    the second beam is hollowed to receive a second portion of the spring; and, the first portion of the spring and the second portion of the spring are interconnected via a U-shaped segment of the spring; wherein the endoscopic grasper includes a rigid chassis coupled to the tissue occlusion device via the line; wherein the rigid chassis comprises a first retainer bar and a second retainer bar; the first retainer bar is oriented to overlap and be parallel to the first beam; and, the second retainer bar is oriented to overlap and be parallel to the second beam.

12. The occlusion combination of claim 11, wherein the line comprises suture.

\* \* \* \* \*